United States Patent [19]

Yamada et al.

[11] 4,284,577
[45] Aug. 18, 1981

[54] NOVEL VITAMIN D₃ DERIVATIVE AND PROCESS FOR PREPARING THE SAME

[75] Inventors: Sachiko Yamada, 1227-4-1218, Hatsuzawamachi, Hachioji-shi, Tokyo, Japan; Masayuki Ohmori, Sagamikomachi, Japan; Hiroaki Takayama, 2-6-12-31, Hatagaya, Shibuya-ku, Tokyo, Japan

[73] Assignees: Sachiko Yamada; Hiroaki Takayada, both of Tokyo, Japan

[21] Appl. No.: 119,390

[22] Filed: Feb. 7, 1980

[30] Foreign Application Priority Data

Feb. 16, 1979 [JP] Japan .................................. 54-16000
Feb. 19, 1979 [JP] Japan .................................. 54-17220

[51] Int. Cl.³ ................................................ C07J 9/00
[52] U.S. Cl. ............................. 260/397.2; 260/239.5; 260/397.1; 260/239.55 R
[58] Field of Search ..................................... 260/397.2

[56] References Cited

U.S. PATENT DOCUMENTS

| | | | |
|---|---|---|---|
| 3,901,928 | 8/1975 | Hesse et al. | 260/397.2 |
| 3,929,770 | 12/1975 | Ishikawa et al. | 260/397.2 |
| 4,196,133 | 4/1980 | De Luca et al. | 260/397.2 |
| 4,201,881 | 5/1980 | De Luca | 568/819 |

FOREIGN PATENT DOCUMENTS

| | | | |
|---|---|---|---|
| 50-12069 | 9/1975 | Japan | 260/397.2 |
| 52-36654 | 7/1977 | Japan | 260/397.2 |
| 52-71456 | 7/1977 | Japan | 260/397.2 |
| 53-71055 | 4/1978 | Japan . | |

1455909 11/1976 United Kingdom .................. 260/397.2

OTHER PUBLICATIONS

Tetrahedron Letters, No. 13 (1977), pp. 1107–1108.
Tetrahedron Letters, No. 27 (1977), pp. 2315–2316.
Steroid, vol. 32 (1978), pp. 453–466.
Biochemistry, vol. 17, pp. 2387–2391 (1978).

Primary Examiner—Elbert L. Roberts
Attorney, Agent, or Firm—Browdy and Neimark

[57] ABSTRACT

A novel vitamin D₃ derivative of the formula

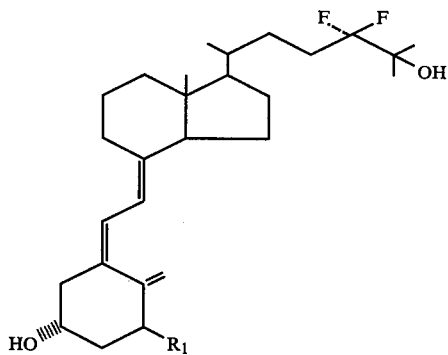

(wherein R₁ is hydrogen or a hydroxyl group) which exhibits strong biological activity like that of vitamin D and is useful as a medicine; and a process for producing the same are disclosed.

2 Claims, No Drawings

NOVEL VITAMIN $D_3$ DERIVATIVE AND PROCESS FOR PREPARING THE SAME

This invention relates to a novel vitamin $D_3$ derivative of the formula:

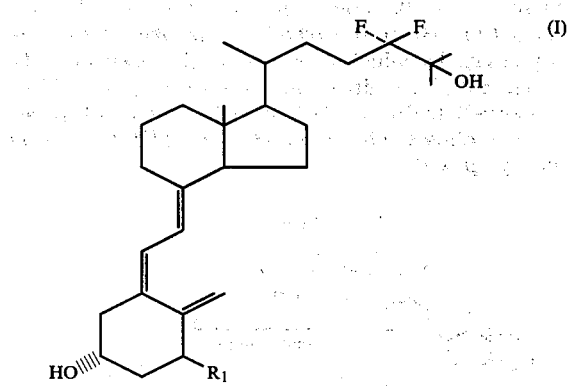

(wherein $R_1$ is hydrogen or a hydroxyl group) and a process for preparing such derivative.

The compound (I) of this invention is prepared by first irradiating a provitamin $D_3$ derivative of the formula:

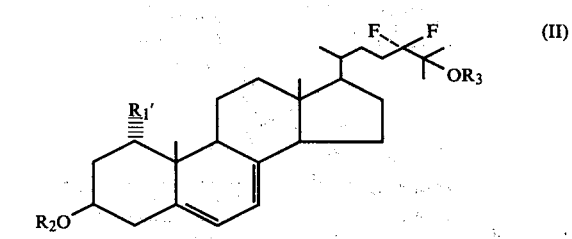

(wherein $R'_1$ is hydrogen or -$OR_4$, $R_4$ being hydrogen or a hydroxyl-protecting group and, $R_2$ and $R_3$ which may be the same or different, represent hydrogen or a hydroxyl-protecting group) with ultraviolet rays to form a previtamin $D_3$ derivative of the formula:

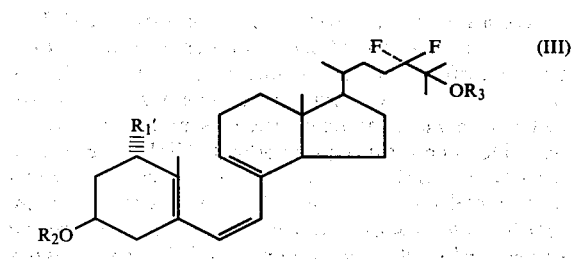

(wherein $R'_1$, $R_2$ and $R_3$ each have the same meaning as defined above), and then isomerizing the derivative (III) thermally to form a vitamen $D_3$ derivative of the formula:

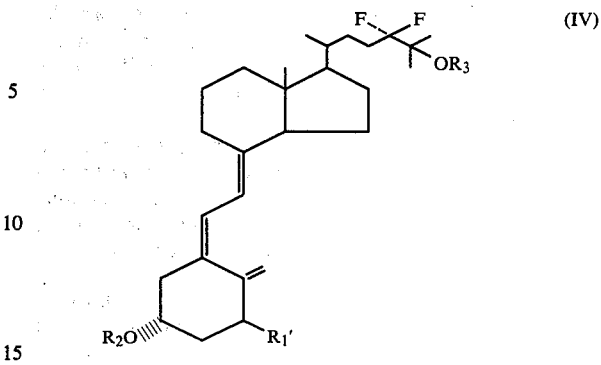

(wherein $R'_1$, $R_2$ and $R_3$ each have the same meaning as defined above), followed by optional removal of the hydroxyl-protecting group.

Common protecting groups may be used as the hydroxyl-protecting groups $R_2$, $R_3$ and/or $R_4$ on the condition that they do not inhibit the reaction induced by UV-irradiation or the isomerization reaction. Protecting groups that can be easily eliminated by simple means are preferred. Generally, acyl groups such as substituted or unsubstituted benzoyl group and acetyl group are used.

The process for preparing the compound (I) according to this invention is hereunder described in detail.

The reaction by irradiation of the provitamin $D_3$ derivative of formula (II) with UV-irradiation to form the previtamin $D_3$ derivative of formula (III) is preferably performed in a solvent. Illustrative solvents are saturated or unsaturated hydrocarbons, ethers and alcohols, and low-boiling solvents are preferred. Illustrative hydrocarbon solvents are hexane and octane; illustrative ether solvents are diethyl ether and tetrahydrofuran; illustrative alcohols are lower alcohols, preferably methanol. Such solvents may be used independently or as a mixture. The reaction induced by the irraidation is preferably performed at a temperature close to room temperature in an inert gas atmosphere such as argon. UV-irradiation sources may be selected from conventional means such as low pressure, medium pressure and high pressure immersion mercury lamps. The irradiation period varies with the intensity of light source, the distance from the source and the scale of the reaction, and it is suitable selected from the range of from several seconds to several hours.

The previtamin $D_3$ derivative of formula (III) thus formed may be isolated by a conventional method, for example, concentration followed by chromatography. Alternatively, the crude derivative may be transferred to the next step without being isolated.

The previtamin $D_3$ derivative of formula (III) can be altered to the vitamin $D_3$ derivative of formula (IV), and the two derivatives are in a thermal equilibrium. Therefore, the compound of formula (IV) can be obtained by isomerizing the compound of formula (III) thermally. Isomerization of the compound (III) may be carried out in a conventional manner, for example, by letting the compound stand at ambient temperature in a solvent or heating it in a solvent. Suitable solvents include common solvents inert to the reaction such as hydrocarbons, ethers, alcohols and benzenes. Preferred solvents are those which boil at low temperatures and have high ability to dissolve the compound of formula (III), for example, hexane, isooctane, benzene, toluene, diethyl ether and tetrahydrofuran, which may be used independently or as a mixture. The reaction time depends on the reaction temperature and is suitably selected from several minutes to several weeks. The isomerization of compound (III) is preferably carried out in an inert gas atmosphere such as argon.

The vitamin $D_3$ derivative of formula (IV) may be isolated from the reaction mixture by common purifying means such as extraction, recrystallization, column chromatography, preparative high-pressure liquid chromatography and preparative thin-layer chromatography.

The thus obtained vitamin $D_3$ derivative of formula (IV) is the same as the compound (I) of this invention if $R_2$, $R_3$ and $R_4$ of formula (IV) are each a hydrogen atom. If at least one of these groups is a hydroxyl-protecting group, it is eliminated to produce the compound (I) of this invention.

Different hydroxyl-protecting groups are removed by different methods. If the protecting group is an acyl group, it may be eliminated by the conventional deacylation technique using, say, a basic substance or a hydrogenated metal. Illustrative basic substances are alkali metal hydroxides, such as potassium hydroxide and sodium hydroxide which are preferred. Illustrative hydrogenated metals are lithium aluminum hydride, lithium borohydride and sodium borohydride. The deacylation is preferably carried out in a solvent. The applicable solvent is suitably selected depending upon the type of a deacylating agent used; if an alkali metal hydroxide is used as deacylating agent, water, alcohol or mixtures thereof with another solvent such as ether are used. For reductive deacylation using a hydrogenated metal, an ether solvent is advantageously used, such as diethyl ether, tetrahydrofuran, 1,2-dimethoxyethane, diglyme, or mixtures thereof. If the deacylating agent is sodium borohydride, an alcohol such as methanol or ethanol may also be used with advantage. The reaction temperature varies with the type of deacylating agent, and is suitably selected from the range of from room temperature to the boiling temperature of the reaction mixture; when an alkali metal hydroxide is used as deacylating agent, the preferred reaction temperature does not exceed 100° C.

The compound of formula (I) can be isolated and purified by a conventional technique, such as extraction, recrystallization, and chromatography, which may be used independently or in combination.

The compound of formula (I) of this invention exhibits strong biological activity like that of vitamin D and it is useful as a medicine.

The provitamin $D_3$ derivative of formula (II) used as the starting material is a novel compound, and it can be prepared from a compound of the formula:

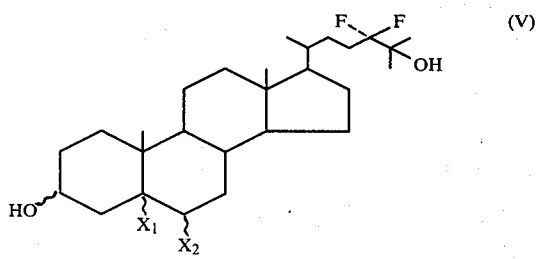

(wherein $X_1$ and $X_2$ each represent hydrogen or, when taken together, form a carbon-carbon bond).

Examples of the compound of formula (V) are 24,24-difluoro-5β-cholestan-3α,25-diol (Va) and 24,24-difluoro-25-hydroxycholesterol (Vb), and these compounds can be readily converted to 24,24-difluoro-25-hydroxy-1,4-cholestadien-3-one (VI) and 24,24-difluoro-25-hydroxy-1,4,6-cholestatrien-3-one (VII), respectively, by a known method, say, the method described in Japanese Patent Disclosure No. 36654/77.

The provitamin $D_3$ derivative of formula (II) is synthesized from the compound (V), (VI) or (VII) by a route (A), (B) or (C) which is described hereunder. Route (A) by which a provitamin $D_3$ derivative (II) wherein $R'_1$ is a hydroxyl group is prepared from 24,24-difluoro-25-hydroxy-1,4-cholestadien-3-one (VI) is outlined as follows, wherein Ac of formula (IIa) represents an acyl group.

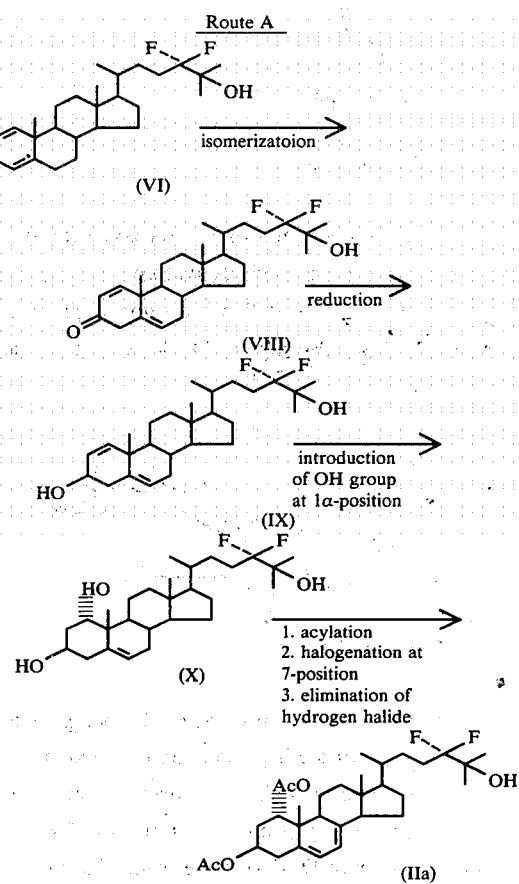

According to this route A, the compound (VI) is isomerized in a solvent such as ether, isopropyl ether, tetrahydrofuran, dimethyl sulfoxide, tert-butyl alcohol or a mixture thereof with the aid of an organic base, for instance, a metal alkoxide such as potassium-tertiary butoxide. The resulting compound (VIII) is converted to a compound (IX) either by reduction with a hydrogenated metal such as lithium aluminum hydride, lithium borohydride or sodium borohydride in an inert organic solvent or by subjecting compound (VIII) to the Meerwein-Ponndorf reduction system using isopropanol-aluminum isopropoxide. A hydroxyl group can be introduced at 1α-position of the compound (IX) by, for example, using a mercuric salt of an organic strong acid (as taught in Japanese Patent Disclosure No. 71456/77) or by hydroboration (as taught in Japanese Patent Disclosure No. 12069/75). The so obtained compound (X) has free hydroxyl groups at both 1- and 3-positions protected with an acyl or other suitable protecting groups before it is converted to a starting material (IIa) of formula (II) wherein $R_2$ and $R_4$ are each a hydroxyl-protecting group and $R_3$ is a hydrogen atom, by the steps of halogenation of 7-positioned carbon and elimination of hydrogen halide.

The compound (IIa) is deacylated in a conventional manner to form a compound (IIb) of formula (II) wherein $R_2$, $R_3$ and $R_4$ are each hydrogen. Alternatively, the compound (IIa) may be acted upon by 1,2,4-triazoline-3,5-dione derivative of the formula:

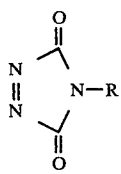

(XI)

(wherein R is an organic residue) to form a 1,4-adduct of the formula:

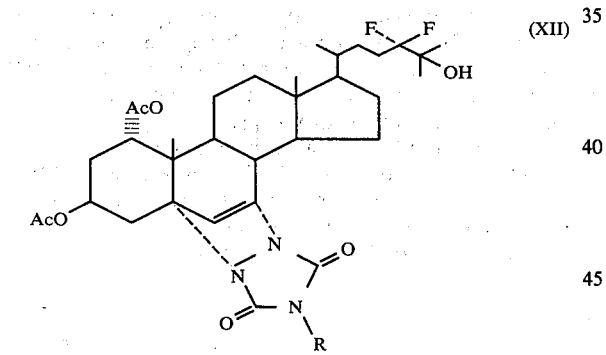

(XII)

(wherein R has the same meaning as defined above), which is then reductively deacylated with a hydrogenated metal, such as lithium aluminum hydride, to form a compound (IIb) of formula (II). The alternative method is advantageous in that the compound (IIa) prepared from the compound (X) in the manner described above can be used without being isolated from the reaction mixture and that a compound (IIb) of high purity can be produced with efficiency. Route (B) by which a provitamin $D_3$ derivative (II) wherein $R'_1$ is a hydroxyl group is prepared from 24,24-difluoro-25-hydroxy-1,4,6-cholestatrien-3-one (VII) is outlined as follows.

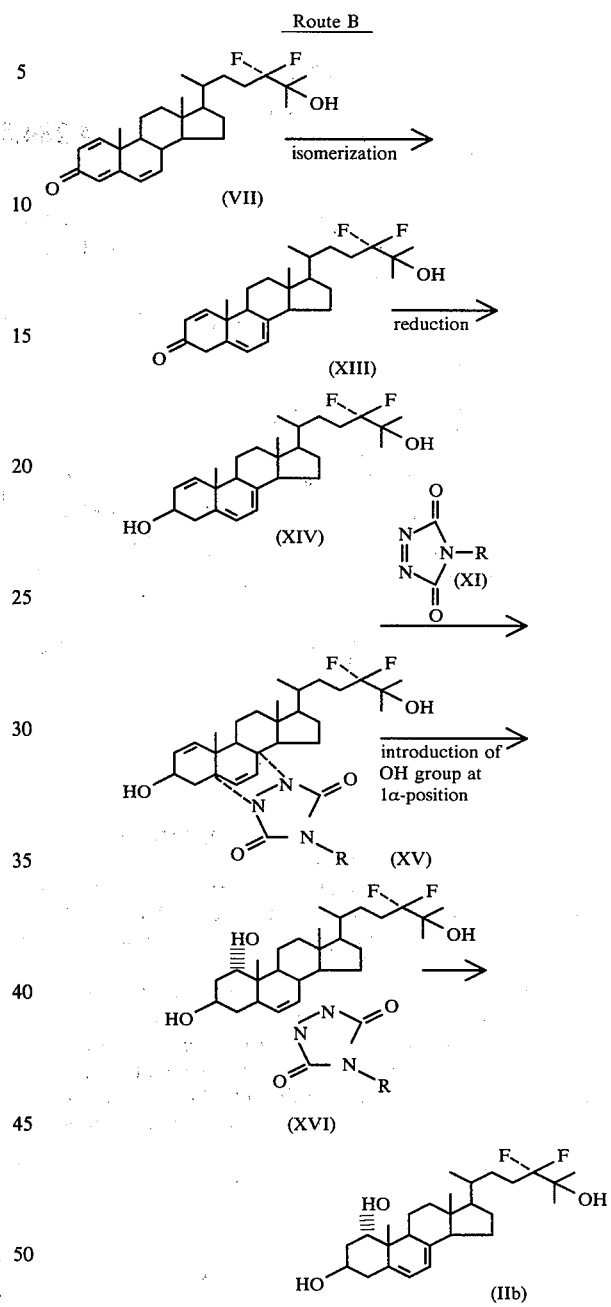

This route B can be followed by performing the method described in Japanese Patent Disclosure Nos. 84560/75 and 84555/75. The compound (XV) may be produced by the method of Japanese Patent Disclosure No. 71055/78 from 24,24-difluoro-25-hydroxycholesta-1,5-diene acylate prepared by acylation of the compound (IX) obtained by the route A. Route (C) by which a provitamin $D_3$ derivative (II) wherein $R_1'$ is hydrogen is prepared from 24,24-difluoro-25-hydroxycholesterol (Vb) is outlined as follows, wherein Ac and R each have the same meaning as defined above.

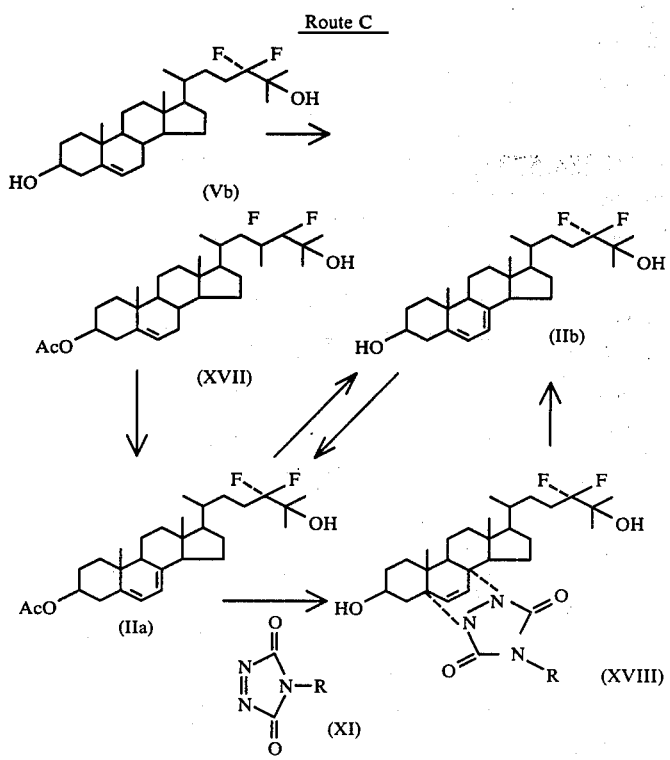

According to this route C, the compound of formula (IIb) can be prepared from the compound of formula (IIa) in a conventional manner, for example, by hydrolysis using an alkali metal hydroxide, or by reductive deacylation with a hydrogenated metal such as lithium aluminum hydride.

Alternatively, the compound of formula (IIa) may be acted upon by 1,2,4-triazoline-3,5-dione derivative of the formula (XI) to form a 1,4-adduct of formula (XVIII), which is then reductively deacylated with a hydrogenated metal such as lithium aluminum hydride to form the compound of formula (IIb). This method is advantageous in that a compound (IIb) of high purity can be produced with high efficiency from a crude product (IIa) that is obtained through halogenation of the carbon atom at 7-position of the compound (XVII) followed by elimination of the hydrogen halide. The compound (IIa) may also be prepared by acylating the compound (IIb) in a conventional manner.

The compound of formula (V) can be produced from methyl lithocholate, methyl-3β-hydroxy-5-cholenate, lower alkyl ester of 3β-hydroxy-5-homocholenic acid, etc. by the following routes D, E and F.

Route D

Preparation of compound (V) from methyl lithocholate

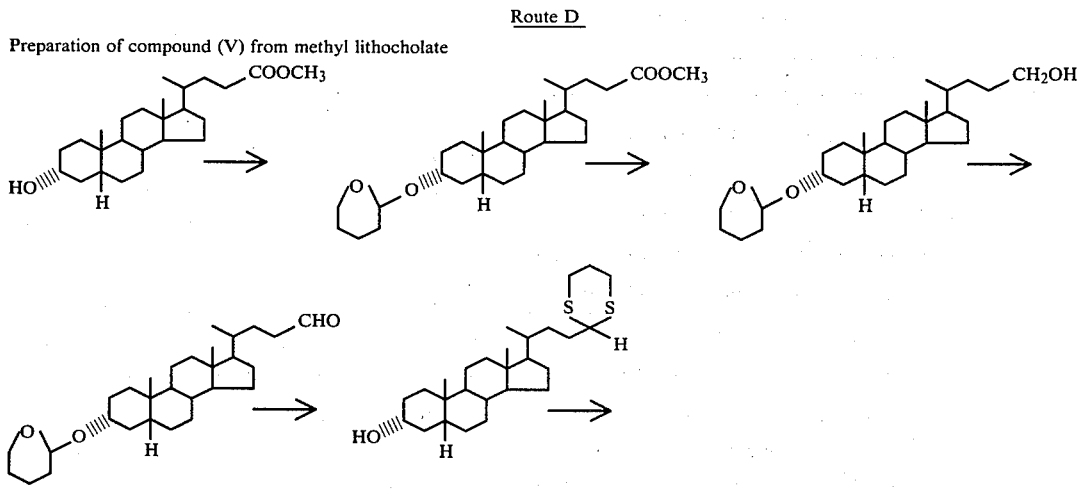

-continued
Route D
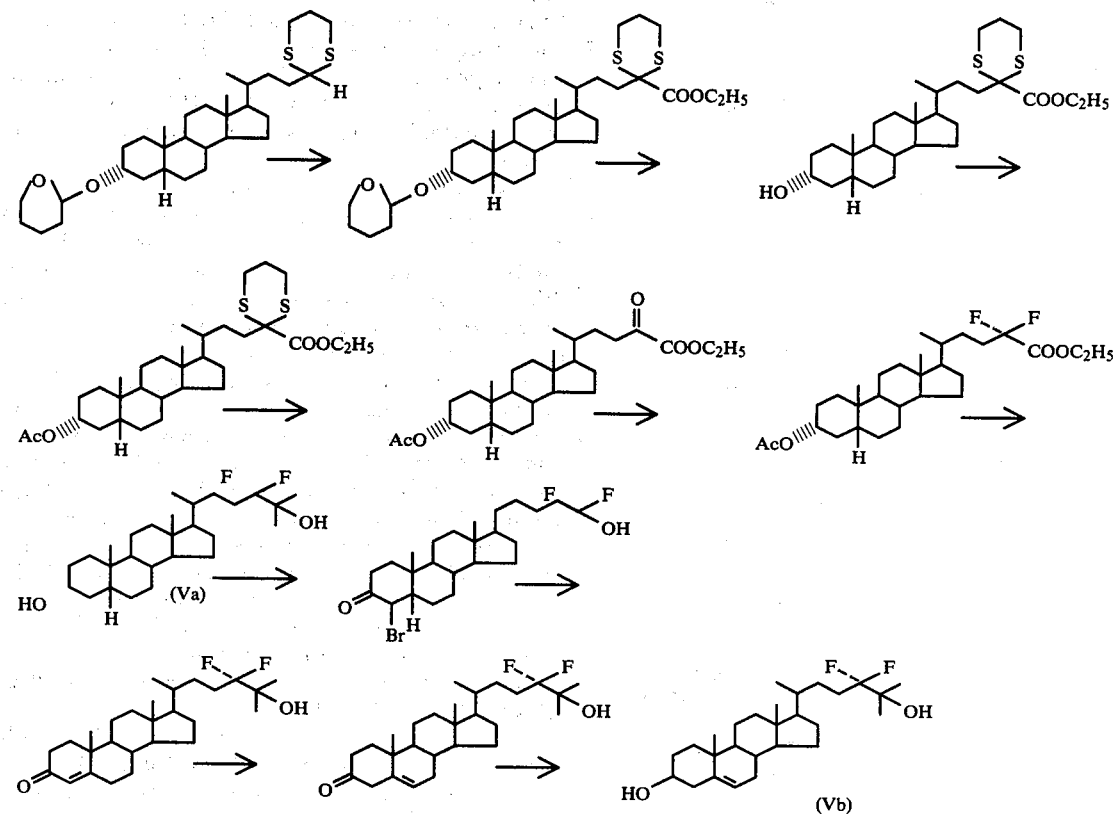
Route E
Preparation of compound (V) from methyl 3β-hydroxy-5-cholenate:
reacted as in Route D
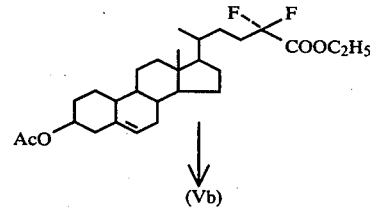
-continued
Route E
(Vb)
Route F
Preparation of compound (V) from methyl 3β-hydroxy-5-homocholenate
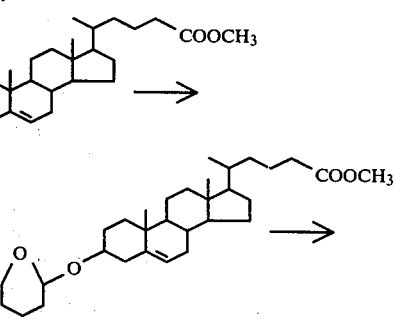

-continued
Route F

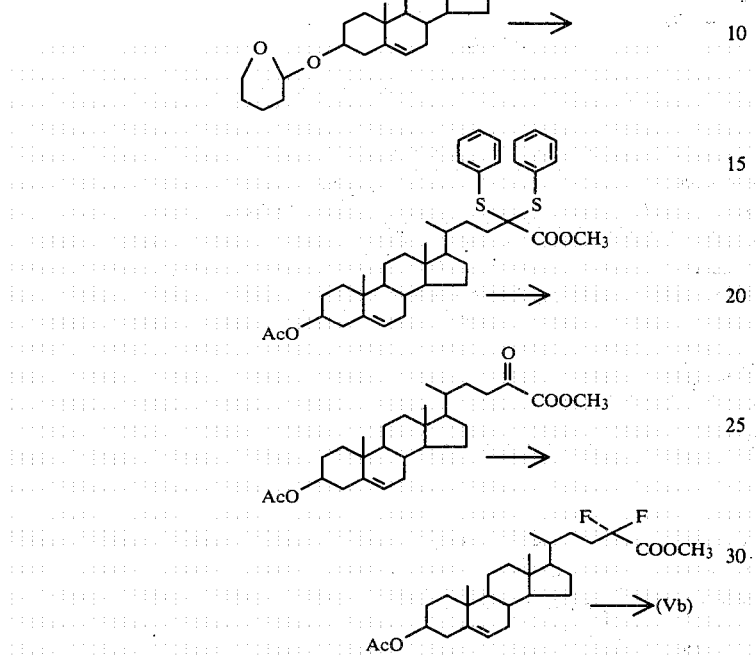

In the process following the routes D, E and F, the reaction for difluorinating at 24-position of ketocarboxylic acid, such as ethyl 3α-acetoxy-24-oxo-5β-homocholanate, methyl 3β-acetoxy-24-oxo-5β-homocholenate and ethyl 3β-acetoxy-24-oxo-5β-homocholenate to form the corresponding 24,24-difluoro compound is performed in an inert organic solvent such as benzene, diglyme or dichloromethane using diethyl aminosulfate trifluoride. There is no particular limitation on the reaction temperature, but an advantageous result can be obtained with low temperature. The reaction time is suitably selected from the range of several tens of minutes to several hours. The reaction for converting the corresponding 24,24-difluoro compound to a 25-hydroxy compound such as 24,24-difluoro-5β-cholestane-3α,25-diol or 24,24-difluoro-25-hydroxy-cholesterol is performed in an inert organic solvent such as tetrahydrofuran, diethyl ether, diglyme or benzene using a methyl metal such as methyllithium or methylmagnesium bromide.

Details of the reactions following the routes (A) thru (F) are described in the following examples of synthesis. The respective end compounds can be isolated from the reaction mixture in a conventional manner.

REFERENCE EXAMPLE 1

Preparation of 24,24-difluoro-5β-cholestane-3α,25-diol (Va) and 24,24-difluoro-25-hydroxycholesterol (Vb) from methyl lithocholate:

(a) A mixture of 970 mg of methyl lithocholate and 474 μl of dihydropyran was dissolved in 1.5 ml of dichloromethane. To the solution, 62.3 mg of pyridinium p-toluenesulfonate was added, and the resulting reaction mixture was let stand for an hour. Dichloromethane (25 ml) was added to the reaction mixture, which was then washed with saturated aqueous sodium chloride, the organic layer was dried over anhydrous potassium carbonate, and the solvent was distilled off. The resulting colorless oily substance was purified by column chromatography (15 g of silica gel, hexane/ethyl acetate =10:1) to produce 1165 mg of methyl 3-O-(2-tetrahydropyranyl)-lithocholate (VI) as a colorless oily substance.

IR spectrum $\nu_{max}$ (cap): 1730 cm$^{-1}$

NMR spectrum δ (ACDl$_3$): 0.63 (3H,s), 0.90 (3H,s), 3.2–4.2 (3H,m), 3.33 (3H,s), 4.72 (1H,m, ω/2=6 Hz)

(b) To a suspension of 32 mg of lithium aluminum hydride in 1.5 ml of tetrahydrofuran, a solution of 389 mg of methyl 3-0-(2-tetrahydropyranyl)-lithocholate in 5 ml of tetrahydrofuran was added dropwise at 0° C. in an argon stream under stirring. After stirring at 0° C. for 10 minutes and stirring at room temperature for 30 minutes, 0.15 ml of water was added dropwise to the reaction mixture at 0° C. under stirring, threby decompose excess reagent which was then filtered off. The filtrate was concentrated under vacuum, and the resulting colorless oily substance was purified by column chromatography (6 g of silica gel, hexane/ethyl acetate =10:3) to produce 358 mg of 3α-(2-tetrahydropyranyloxy)-24-hydroxy-5β-cholane as a white powder.

IR spectrum $\nu_{max}$ (CHCl$_3$): 3480 cm$^{-1}$

NMR spectrum δ (CDCl$_3$: 0.65 (3H,s), 0.90 (3H,s), 3.2–4.0 (5H,m), 4.75 (1H,m, ω/2=6 Hz)

(c) A suspension comprising a mixture of 221 mg of pyridinium chlorochromate (C$_5$H$_5$N$^+$HCrO$_3$Cl$^-$) and 8.3 mg of sodium acetate in 1 ml of dichloromethane was prepared. To the suspension, a solution of 221 mg of 3α-(2-tetrahydropyranyloxy)-24-hydroxy-5β-cholane in 4 ml of dichloromethane was added at one time in an argon stream under stirring. After stirring for 3 hours, the supernatant of the reaction mixture was separated by decantation, and the precipitate was washed with dichloromethane three times. The supernatant was combined with the washings, passed through a short column with silica gel (4 g). The eluate with dichloromethane was concentrated under vacuum. 3α-(2-Tetrahydropyranyloxy)-24-oxo-5β-cholane (177 mg) was obtained as a colorless oily substance.

IR spectrum $\nu_{max}$ (CHCl$_3$): 1715 cm$^{-1}$

NMR spectrum δ (CDCl$_3$): 0.65 (3H,s) 0.97 (3H,s), 3.3–4.2 (3H,m), 4.75 (1H,m, ω/2=6 Hz), 9.82 (1H,t,J=2 Hz)

(d) To a solution of 19.3 g of 3α-(2-tetrahyropyranyloxy)-24-oxo-5β-cholane and 8.92 of 1,3-propanediol in 100 ml of dichloromethane, 560 μl of boron trifluoride etherate was added at −78° C. in an argon stream under stirring that continued for 15 minutes. After stirring at room temperature for 3 hours, the reaction mixture was washed sequentially with 10% aqueous potassium hydroxide, water and saturated aqueous sodium chloride, the organic layer was dried over anhydrous magnesium sulfate and the solvent was distilled off. The residue was dissolved in 15 ml of ethyl acetate. To the solution, 30 ml of hexane was added. The solution was then let stand at −10° C. for 4 hours. The precipitating crystal was filtered. 3α-Hydroxy-24,24-propylenedithio-5β-cholane (9.6 g) was obtained as colorless needles.

Melting point: 145°–146° C. (recrystallized from hexane/ethyl acetate =10:3)

IR spectrum $\nu_{max}$ (KBr): 3300 cm$^{-1}$

NMR spectrum δ (CDCl$_3$): 0.63 (3H,s), 0.92 (3H,s), 2.5–3.1 (4H,m), 3.60 (1H,m, ω/2=15 Hz), 3.98 (1H,t,J=6 Hz)

(e) To a solution of 4.8 g of 3α-hydroxy-24,24-propylenedithio-5β-cholane and 1.53 ml of dihydrofuran in 15 ml of dichloromethane, 266 mg of pyridinum p-toluenesulfonate was added. After standing for 2 hours, 50 ml of dichloromethane was added to the reaction mixture. The organic layer was washed with saturated aqueous sodium chloride and dried over anhydrous magnesium sulfate. The residue obtained by distilling the solvent off was purified by column chromatography (120 g of silica gel, hexane/ethyl acetate =10:1). 3α-(2-Tetrahydropyranyloxy)-24,24-propylenedithio-5β-cholane (3.5 g) was obtained as a white powder.

(f) To a solution of 12 g of 3α-(2-tetrahydropyranyloxy)-24,24-propylenedithio-5β-cholane in 40 ml of tetrahydrofuran, 16.4 ml of hexane containing 15% of n-butyllithium was added dropwise at −20° C. in an argon stream under stirring. After stirring for 2 hours, the reaction mixture was added dropwise to 43 ml of ethyl chlorocarbonate over a period of 10 minutes at −78° C. in an argon stream under stirring. After stirring at room temperature for 2 hours, the reaction mixture was filtered and the filtrate was concentrated under vacuum. The resulting oily residue was purified by column chromatography (1200 g of silica gel), hexane/ethyl acetate =10:1) to recover 1.8 g of the starting material and obtain 8.85 g of a white powder of ethyl 3α-(2-tetrahydropyranyloxy)-24,24-propylenedithio-5β-homocholanate.

IR spectrum $\nu_{max}$ (CHCl$_3$): 1720 cm$^{-1}$

NMR spectrum δ (CDCl$_3$): 0.63 (3H,s), 0.91 (3H,s), 1.34 (3H,t,J =6.5 Hz), 4.27 (2H,q,J =6.5 Hz) 4.74 (1H,m, ω/2=6 Hz)

(g) To a solution of 493 mg of ethyl 3α-(2-tetrahydropyranyloxy)-24,24-propylenedithio-5β-homocholanate in 10 ml of ethanol, 21 mg of pyridinium p-toluenesulfonate was added at 55° C. under stirring for 3 hours. The reaction mixture was then concentrated under vacuum, and the residue was purified by column chromatography (10 g of silica gel, hexane/ethyl acetate =5:2). Ethyl 3α-hydroxy-24,24-propylenedithio-5β-homocholanate (428 mg) was obtained as colorless crystals.

IR spectrum $\nu_{max}$ (CHCl$_3$): 1715 cm$^{-1}$

NMR spectrum δ (CDCl$_3$): 0.64 (3H,s), 0.93 (3H,s), 1.34 (3H,t,J =7 Hz), 4.28 (2H,q,J =7 Hz)

(h) To a solution of 428 mg of ethyl 3α-hydroxy-24,24-propylenedithio-5β-homocholanate in 5 ml of pyridine, 2 ml of acetic anhydride was added at 0° C. under stirring. After standing at room temperature for 14 hours, the reaction mixture was poured into 30 ml of 2 N hydrochloric acid and extracted with ethyl acetate. The organic layer was washed sequentially with 2 N hydrochloric acid, water, saturated aqueous sodium bicarbonate and saturated aqueous sodium chloride, and dried over anhydrous magnesium sulfate. After distilling the solvent off, the residue was purified by column chromatography (120 g of silica gel, hexane/ethyl acetate =5:1) to give 417 g of colorless crystals of ethyl 3α-acetoxy-24,24-propylenedithio-5β-homocholanate.

IR spectrum $\nu_{max}$ (CHCl$_3$): 1715, 1720 (sh) cm$^{-1}$

NMR spectrum δ(CDCl$_3$): 0.64 (3H,s), 0.93 (3H,s), 1.34 (3H,t,J =7 Hz), 2.04 (3H,s), 2.3–3.2 (4H,m), 4.30 (2H,q,J=7 Hz), 4.73 (1H,m, ω/2=20 Hz)

(i) To a solution of 847 mg of N-bromosuccinimide in 20 ml of 95% aqueous acetone, a solution of 336 mg of ethyl 3α-acetoxy-24,24-propylenedithio-5β-homocholanate was added at 0° C. under stirring for 15 minutes. The reaction mixture was poured into 50 ml of saturated aqueous sodium hydrogen sulfite and extracted with a mixture of hexane and dichloromethane (1:1). The separating organic layer was washed twice with 30 ml of saturated aqueous sodium bicarbonate and once with 50 ml of saturated aqueous sodium chloride. The washings were further extracted with 20 ml of a mixture of hexane and dichloromethane (1:1) twice, followed by washing with saturated aqueous sodium chloride. The resulting organic layer was combined with the previously separated organic layer, and the combined organic layers were washed with saturated aqueous sodium chloride again and dried over anhydrous magnesium sulfate. The solvent was distilled off and the resulting residue was purified by column chromatography (hexane/ethyl acetate =6:1) to give 254 mg of colorless crystals of ethyl 3α-acetoxy-24-oxo-5β-homocholanate.

IR spectrum $\nu_{max}$ (CHCl$_3$): 1720 cm$^{-1}$

NMR spectrum δ (CDCl$_3$): 0.64 (3H,s), 0.94 (3H,s), 1.37 (3H,t,J =7 Hz), 2.64 (3H, s), 1.78 (2H,bs, ω/2=15 Hz), 4.34 (2H,q,J =7 Hz), 4.78 (1H,m, ω/2=20 Hz)

(j) To a solution of 3.3 ml of diethylaminosulfur trifluoride, (C$_2$H$_5$)$_2$NSF$_3$, produced from N,N-diethylaminotrimethylsilane and sulfur tetrafluoride in 20 ml of dichloromethane, a solution of 5.5 g of ethyl 3α-acetoxy-24-oxo-5β-homocholanate in 60 ml of dichloromethane was added at −78° C. in an argon stream under stirring. After standing at room temperature for 3 hours, the reaction mixture was poured into a mixture of 200 ml of saturated aqueous medium bicarbonate and 150 ml of hexane under vigrous stirring. The separating organic layer was sequentially washed with saturated aqueous medium bicarbonate and saturated sodium chloride, and dried over anhydrous magnesium sulfate. The solvent was distilled off and the resulting residue was purified by column chromatography (100 g of silica gel, hexane/ethyl acetate =10:1) to recover 700 mg of the starting material and obtain 3.7 g of ethyl 3α-acetoxy-24,24-difluoro-5β-homocholanate was colorless oily substance.

IR spectrum $\nu_{max}$ (CHCl$_3$): 1775, 1720 cm$^{-1}$

NMR spectrum δ (CDCl$_3$): 0.65 (3H,s), 0.93 (3H,s), 1.36 (3H,t,J=7 Hz), 2.03 (3H,s), 4.35 (2H,q,J=7 Hz), 4.73 (1H,m, ω/2=20 Hz)

(k) To 970 μl of a solution of methylmagnesium bromide in tetrahydrofuran (1 mol/l), a solution of 60 mg of ethyl 3α-acetoxy-24,24-difluoro-5β-homocholanate in 1 ml of tetrahydrofuran was added dropwise at 0° C. in an argon stream under stirring. After stirring at room temperature for 30 minutes, 10 ml of 2 N hydrochloric acid was added to the reaction mixture at 0° C. under stirring. After stirring for 5 minutes, the reaction mixture was extracted with ethyl acetate. The separating organic layer was sequentially washed with 2 N hydrochloric acid, water, saturated aqueous sodium bicarbonate and saturated aqueous sodium chloride, and dried over anhydrous magnesium sulfate. The solvent was distilled off, and the resulting residue was purified by column chromatography (10 g of silica gel, hexane/ethyl acetate=1:1) to obtain 39 mg of 24,24-difluoro-5β-cholestane-3α,25-diol (Va) as colorless crystals.

Melting point: 142° to 142.5° C. (recrystallized from hexane/ethanol=50:1)

IR spectrum $\nu_{max}$ (CHCl$_3$): 3620, 3450 cm$^{-1}$

NMR spectrum δ (CDCl$_3$): 0.66 (3H,s), 0.92 (3H,s), 1.31 (6H,s), 3.65 (1H,m, ω/2=18 Hz)

Mass spectrum m/e: 440 (M+), 423, 422 (base peak)

(1) To a solution of 800 mg of 24,24-difluoro-5β-cholestane-3α,25-diol (Va) in 32 ml of tert-butyl alcohol, 15 ml of water, 200 μl of 48% hydrobromic acid and 800 mg of N-bromoacetamide were added. After stirring at room temperature for 3 days, ethyl acetate was added to the reaction mixture, which was then washed sequentially with 0.5% aqueous sodium thiosulfate and saturated aqueous sodium chloride, and dried over anhydrous magnesium sulfate. The solvent was distilled off, and the resulting residue was purified through a short column (5 g of silica gel) to produce 950 mg of a crude product. The product was recrystallized from ether/hexane to produce 4β-bromo-24,24-difluoro-25-hydroxy-5β-cholestan-3-one.

Melting point: 152° to 153° C.

NMR spectrum δ (CDCl$_3$): 0.70 (3H,s), 1.10 (3H,s), 1.30 (6H,s), 5.00 (1H,d,J=13 Hz)

Mass spectrum m/e: 519, 517 (+), 438

(m) To a solution of 950 mg of 4β-bromo-24,24-diluoro-25-hydroxy-5β-cholestan-3-one in 15 ml of dimethylformamide, 500 mg of lithium carbonate was added. The reaction mixture was heated under reflux for 2 hours with stirring. After cooling, about 100 ml of water was added to the reaction mixture. The precipitating crystal was filtered, washed with water and dried to obtain 730 mg of a crude enone compound. The compound was purified by column chromatography (40 g of silica gel, hexane/ethyl acetate=7:3) to obtain 498 mg of 24,24-difluoro-25-hydroxy-4-cholesten-3-one as crystals.

Melting point: 177° to 178° C., (recrystallized from ether/hexane)

NMR spectrum δ (CDCl$_3$): 0.70 (3H,s), 1.16 (3H,s), 1.32 (6H,s), 5.77 (1H,s)

Mass spectrum m/e: 436 (M+), 394

(n) 24,24-Difluoro-25-hydroxy-4-cholesten-3-one (457 mg) was added to 46 ml of ether and 650 ml of dimethyl sulfoxide. After stirring at 10° C. for 15 minutes, the reaction mixture was poured into ice water saturated with carbon dioxide gas, and extracted with ethyl acetate after vigorous stirring. The separating organic layer was washed with water, and dried over anhydrous magnesium sulfate. By distilling the solvent off, a crude crystal of 24,24-difluoro-25-hydroxy-5-cholesten-3-one was obtained.

NMR spectrum δ (CDCl$_3$): 0.70 (3H,s), 1.20 (3H,s), 1.30 (6H,s), 5.35 (1H,m)

The crude product was dissolved in a mixture of 13 ml of ether and 25 ml of methanol. To the solution, 10 ml of an aqueous solution containing 200 mg of sodium borohydride was added at 0° C. After stirring at 0° C. for 1 hour, the reaction mixture was extracted with ethyl acetate. The separating organic layer was washed with 1% hydrochloric acid and saturated aqueous sodium chloride, and dried over anhydrous magnesium sulfate. After distilling the solvent off, the resulting residue was purified by column chromatography (15 g of silica gel, hexane/ethyl acetate=2:1) to obtain 320 mg of the crystal of 24,24-difluoro-25-hydroxycholesterol (Vb).

Melting point: 168° to 170° C. (recrystallized from ether)

NMR spectrum δ (CDCl$_3$): 0.70 (3H,s), 0.95 (3H,d,J=6 Hz), 1.02 (3H,s), 1.32 (6H,s), 5.40 (1H,d,J=4 Hz)

Mass spectrum m/e: 438 (M+), 420

REFERENCE EXAMPLE 2

Preparation of ethyl 3β-acetoxy-24-oxo-5-homocholenate from methyl 3β-hydroxy-5-cholenate:

Ethyl 3β-acetoxy-24-oxo-5-homocholenate was prepared by treating methyl 3β-hydroxy-5-cholenate in the same manner as described in Reference Example 1(a) thru (i).

REFERENCE EXAMPLE 3

Preparation of methyl 3β-acetoxy-24-oxo-5-homocholenate from methyl 3β-hydroxy-5-homocholenate:

To a solution of 4 mmol of diisopropylamine in 5 ml of tetrahydrofuran, 1.92 ml of hexane containing 4 mmol of n-butyl lithium was added at 0° C. in argon stream under stirring, and the mixture was stirred at 0° C. for 10 minutes. To the resulting solution of lithium diisopropylamide in hexane, 2.5 ml of tetrahydrofuran containing 4 mmol of methyl 3β-(2-tetrahydropyranyloxy)-5-homocholenate (prepared from methyl 3β-hydroxy-5-homocholenate in the same manner as described in Reference Example (1(a)) was added dropwise at −78° C. over a period of 15 minutes under stirring. After stirring at −78° C. for 30 minutes, 4 mmol of phenyl disulfide in a mixture of 2 ml of tetrahydrofuran and 4 mmol of hexamethylphosphoramide was added dropwise to the reaction mixture over a period of 20 minutes, followed by stirring at −78° C. for 30 minutes. After gradually restoring the temperature of the reaction mixture to room temperature, the mixture was poured into 40 ml of water and extracted with ether. The separating organic layer was washed sequentially with 10% aqueous sodium hydroxide, water, 10% hydrochloric acid and water, and dried over anhydrous magnesium sulfate. By distilling the solvent off, methyl 3β-(2-tetrahydropyranyloxy)-24,24-diphenylthio-5-homocholenate was obtained. By treating the 24,24-diphenylthio compound in the same manner as of Reference 1(g) and (h), methyl 3β-acetoxy-24,24-diphenylthio-5-homocholenate was obtained. The resulting methyl 3β-acetoxy-24,24-diphenylthio-5-homocholenate was heated under reflux in a methanolic iodine solution and treated with aqueous trifluoroacetic acid to obtain methyl 3β-acetoxy-24-oxo-5-homocholenate.

REFERENCE EXAMPLE 4

The crystal of 24,24-difluoro-25-hydroxycholesterol (Vb) was prepared by treating the ethyl 3β-acetoxy-24-oxo-5-homocholenate of Reference Example 2 or the methyl 3β-acetoxy-24-oxo-5-homocholenate of Reference Example 3 in the same manner as of Reference Example 1(j) and (k). In a mixed examination, the melting point of a mixture of the product and the compound prepared in Reference Example 1(n) has the same melting point as that of the compound. The product also had an NMR spectrum and mass spectrum that agree with those of the compound.

REFERENCE EXAMPLE 5

Preparation of 24,24-difluoro-5,7-cholestadine-1α,3β,25-triol from 24,24-difluoro-5β-cholestane-3α,25-diol:

(a) To a solution of 100 mg of 24,24-dilfuoro-5β-cholestane-3α,25-diol in 2 ml of dioxane, 207 mg of 2,3-dichloro-5,6-dicanobenzoquinone was added. The mixture was heated under reflux for 4 hours. After cooling, the reaction mixture was filtered, the filtrate was passed through a short column (4 g of alumina) and eluted with ethyl acetate/ethanol (2:1). After concentrating the eluate under vacuum, the residue was purified by preparative thin-layer chromatography (20 g of silica gel, developed three times with hexane/ethyl acetate=5:2) to produce 45 mg of 24,24-difluoro-25-hydroxy-1,4-cholestadien-3-one (VI) as needles.

Melting point: 176° to 177° C. (recrystallized from hexane/ethyl acetate=1:1)

IR spectrum $\nu_{max}$ (KBr): 3470, 1660, 1615 cm$^{-1}$
UV spectrum $\nu_{max}$ (C$_2$H$_5$OH): 247, 296 mm
NMR spectrum $\delta$ (CDCl$_3$): 0.75 (3H,s), 1.30 (6H,s), 1.57 (3H,s), 6.08 (1H,s), 6.25 (1H,dd,J=10 Hz, 2 Hz), 7.03 (1H,d,J=10 Hz)

(b) To a solution of 513 mg of 24,24-difluoro-25-hydroxy-1,4-cholestadien-3-one (VI) in a mixture of 15 ml of dimethyl sulfoxide and 5 ml of ether, 662 mg of potassium tert-butoxide was added at 15° C. in an argon stream under stirring. After stirring for 30 minutes, the reaction mixture was poured into a mixture of 90 ml of water and 5 g of dry ice uner stirring, and extracted with ether. The separating organic layer was washed with saturated aqueous sodium chloride and concentrated under vacuum. The resulting residue was dissolved in a mixture of 5 ml of ether and 25 ml of methanol. To the solution, 5 ml of an aqueous solution containing 25 mg of sodium borohydride was added at 0° C. under stirring. After stirring for 15 minutes the reaction mixture was poured into 60 ml of 2 N hydrochloric acid and extracted with ethyl acetate. The separating organic layer was washed with saturated aqueous sodium chloride and dried over anhydrous potassium carbonate. After the solvent was distilled off, the residue (474 mg) was purified by column chromatography (20 g of silica gel, hexane/ethyl acetate=2:1) to obtain 252 mg of a white crystalline powder of 24,24-difluoro-1,5-cholestadiene-6$\beta$,25-diol (IX).

Melting point: 170° to 171° C. (recrystallized from hexane/ethyl acetate=4:1)

IR spectrum $\nu_{max}$ (KBr): 3400, 3550 cm$^{-1}$
NMR spectrum $\delta$ (CDCD$_3$): 0.74 (3H,s), 1.12 (3H,s), 1.34 (6H,s), 4.22 (1H, bs, $\omega/2$=18 Hz), 5.4–5.5 (1H,m), 5.59 (1H,d,J=10 Hz), 5.83 (1H,dd,J=10 Hz, 2 Hz)
Mass spectrum m/e: 436 (M$^+$, base peak), 421, 418, 407, 403

(c) To a solution of 445 mg of mercuric acetate in 1.4 ml of water, 1.4 ml of tetrhydrofuran and 108 $\mu$l of trifluoroacetic acid were added at room temperature under stirring. One minute later, a solution of 122 mg of 24,24-difluoro-1,5-cholestadiene-3$\beta$,25-diol (IX) in 1.4 ml of tetrahydrofuran/dimethylformamide (1:1) was added to the previously prepared solution. After stirring for 25 hours, 2 ml of an aqueous solution of 2 N sodium hydroxide as well as 16 mg of sodium borohydride dissolved in 0.7 ml of 2 N aqueous sodium hydroxide was added to the reaction mixture. After stirring for an hour, 2.5 g of potassium carbonate was added to the reaction mixture to separate the organic layer from the aqueous layer, which was extracted five times with 15 ml of tetrahydrofuran. The organic layer was combined with the extracts, and concentrated under vacuum. The resulting residue was dissolved in 30 ml of chloroform, and the solution was washed with saturated aqueous sodium chloride and dried over anhydrous magnesium sulfate. After distilling the solvent off, 15 ml of benzene was added to the residue, and water was removed by azeotropic distillation. The above procedure was repeated five times. Upon drying the residue in a desiccator overnight, 125 mg of a colorless solid was obtained. The solid was dissolved in 1 ml of pyridine, and 1 ml of acetic anhydride was added to the solution at 0° C. under stirring. After standing overnight, the reaction mixture was poured into 30 ml of 2 N hydrochloric acid and extracted with ethyl acetate. The separating organic layer was sequentially with 2 N hydrochloric acid, water, saturated aqueous sodium bicarbonate and saturated aqueous sodium chloride, and dried on anhydrous sodium sulfate. After distilling the solvent off, the resulting colorless oily substance (130 mg) was purified by column chromatography (20 g of silica gel, hexane/ethyl acetate=5:2), whereby 24 mg of 3-acetate was recovered and 40 mg of 1$\alpha$,3$\beta$-diacetoxy-24,24-difluoro-5-cholesten-25-ol was obtained as an oily substance.

NMR spectrum $\delta$ (CDCl$_3$): 0.67 (3H,s), 0.91 (3H,d,J=5 Hz), 1.30 (6H,s), 2.03 (3H,s), 2.08 (3H,s), 4.90 (1H,m), 5.08 (1H,t,J=2 Hz), 5.22 (1H,d,j=4 Hz)
Mass spectrum m/e: 538 (M$^+$), 436, 418 (base peak)

(d) To a solution of 33 mg of 1$\alpha$,3$\beta$-diacetoxy-24,24-difluoro-5-cholesten-25-ol in 1 ml of hexane/benzene (1:1), 13.1 mg of N-bromosuccinimide was added, and the resulting mixture was heated under reflux for 30 minutes in an argon stream. After cooling, the reaction mixture was filtered and the filtrate was concentrated under vacuum. The resulting residue was dissolved in 1 ml of xylene. To the solution, 85 $\mu$l of s-collidine was added and the mixture was heated under reflux for 30 minutes in an argon stream. After cooling, the reaction mixture was poured into 20 ml of 2 N hydrochloric acid and extracted with ethyl acetate. The separating organic layer was washed sequentially with 2 N hydrochloric acid, water, saturated aqueous sodium bicarbonate and saturated aqueous sodium chloride, and dried over anhydours magnesium sulfate. After distilling the solvent off, the resulting pale yellow oily substance (32 mg) was dissolved in 1 ml of ether. To the solution, 7.5 mg of 4-phenyl-1,2,4-triazoline-3,5-dione (XI) was added, and the mixture was let stand in an argon stream overnight at room temperature. The reaction mixture was then purified by preparative thin-layer chromatography (10 g of silica gel, hexane/ethyl acetate=1:1) to obtain 12 mf of a 1,4-adduct (XII) of 1$\alpha$,3$\beta$-diacetoxy-24,24-difluoro-5,7-cholestadien-25-ol with 4-phenyl-1,2,4-triazoline-3,5-dione as crystals.

IR spectrum $\nu_{max}$ (CHCl$_3$): 1730, 1690 cm$^{-1}$
NMR spectrum $\delta$ (CDCl$_3$): 0.80 (3H,s), 1.27 (6H,s), 1.30 (3H,s), 1.99 (3H,s), 2.10 (3H,s), 6.30 (1H,d,J=9 Hz) 6.45 (1H,d,J=9 Hz)

(e) To a suspension of 6.4 mg of lithium aluminum hydride in 0.5 ml of tetrahydrofuran, a solution of 12 mg of the 1,4-adduct (XII) obtained in Reference Example 5(d) in 1 ml of tetrahydrofuran was added dropwise with heating under reflux in an argon stream. After standing for 2 hours, 0.5 ml of water was added dropwise to the mixture at 0° C. under stirring. The resulting mixture was then poured into 2 N hydrochloric acid. After extraction with ethyl acetate, the separating organic layer was washed sequentially with 2 N hydrochloric acid, water, saturated aqueous sodium bicarbonate and saturated aqueous sodium chloride, and dried over anhydrous sodium sulfate. After distilling the solvent off, the resulting residue (12 mg) was purified by preparative thin-layer chromatography (hexane/ethyl acetate=1:2) to obtain 3 mg of the colorless crystal of 24,24-difluoro-5,7-cholestadiene-1$\alpha$,3$\beta$,25-triol (IIb).

IR spectrum $\nu_{max}$ (CHCl$_3$): 3600, 3400 cm$^{-1}$

UV spectrum $\lambda_{max}$ (EtOH): 262, 272, 282.5, 294 nm

NMR spectrum δ (CDCl$_3$): 0.63 (3H,s), 0.97 (3H,d,J=5 Hz), 0.95 (3H,s), 1.31 (6H,s), 3.76 (1H,m, ω/2=7 Hz), 4.06 (1H,m, ω/2=30 Hz), 5.40 (1H,dd,J=5 Hz), 5.65 (1H,d,J=6 Hz)

Mass spectrum m/e: 452 (M+)

(f) 1α,3β-Diacetoxy-24,24-difluoro-5,7-cholestadien-25-ol (IIa) was prepared by acetylating 5 mg of the 24,24-difluoro-5,7-cholestadiene-1α,3β,25-triol (IIb) in a conventional manner using pyridine and acetic anhydride.

UV spectrum $\lambda_{max}$ (EtOH): 262, 272, 282, 294 nm

REFERENCE EXAMPLE 6

(a) To a mixture of 10 ml of acetic anhydride and 1 ml of pyridine, 380 mg of 24,24-difluoro-25-hydroxycholesterol (Vb) was added. After stirring overnight at room temperature, about 50 ml of ice water was added to the reaction mixture, and the solvent was distilled off under vacuum. The precipitating crystal was filtered off, washed with water and dried to give 404 mg of 24,24-difluoro-25-hydroxycholesterol-3-acetate (XVII).

(b) To a solution of 300 mg of 24,24-difluoro-25-hydroxy-cholesterol 3-acetate (XVII) in a mixture of 6 ml of hexane and 1 ml of benzene, 133.5 mg of N-bromosuccinimide was added, and the mixture was heated under reflux in an argon stream for 45 minutes. After cooling, the insoluble crystal was filtered off and washed with hexane. The filtrate was combined with the washings, and the solvent was distilled off. The residue was dissolved in 9 ml of xylene, and s-collidine (798 μl) was added to the solution, which was heated under reflux in an argon stream for 30 minutes. After cooling, ethyl acetate was added to the reaction mixture, which was then washed sequentially with 1% hydrochloric acid and saturated aqueous sodium chloride, and dried over anhydrous sodium sulfate. After distilling the solvent off, the residue was dissolved in 10 ml of ether. To the solution, 4-phenyl-1,2,4-triazoline-3,5-dione (XI) was added in an amount 1.1 times the equivalent (as estimated by UV spectrum) of 3β-acetoxy-24,24-difluoro-5,7-cholestadien-25-ol (IIa) contained in the solution. The mixture was then stirred at 0° C. for 10 minutes. After distilling the solvent off, the residue was purified by column chromatography (30 g of silica gel, hexane/ethyl acetate=2:1) to obtain 177 mg of 1,4-adduct (XVIII) of 3β-acetoxy-24,24-difluoro-5,7-cholestadien-25-ol with 4-phenyl-1,2,4-triazoline-3,5-dione as crystals.

Melting point: 194° to 195° C. (recrystallized from ethyl acetate)

NMR spectrum δ (CDCl$_3$): 0.82 (3H,s), 1.00 (3H,s), 1.32 (6H,s), 2.02 (3H,s), 3.25 (1H,dd,J=14 Hz, 5 Hz), 5.50 (1H,tt,J=10 Hz, 5 Hz), 6.36 (2H, ABq, J=8 Hz)

(c) A solution of 200 mg of 1,4-adduct (XVIII) of 3β-acetoxy-24,24-difluoro-5,7-cholestadien-25-ol with 4-phenyl-1,2,4-triazoline-3,5-dione in 5 ml of tetrahydrofuran was added dropwise to a suspension of 58 mg of lithium aluminum hydride in 5 ml of tetrahydrofuran in an argon stream. The reaction mixture was heated under reflux for 30 minutes. After cooling, wet tetrahydrofuran was added to the mixture to decompose excess reagents. After addition of 5% hydrochloric acid, the mixture was extracted with ethyl acetate. The separating organic layer was washed with water and dried over anhydrous sodium sulfate. The solvent was distilled off, and the resulting residue was purified by column chromatography (10 g of silica gel, hexane/ethyl acetate=1:2) to obtain 97 mg of the crystal of 24,24-difluoro-5,7-cholestadien-3β,25-diol (IIb).

Melting point: 177° to 179° C. (recrystallized from ether)

NMR spectrum δ (CDCl$_3$): 0.63 (3H,s), 0.94 (3H,s), 1.31 (6H,s), 3.60 (1H,m), 5.40 (1H,m), 5.60 (1H,dd,J=6 Hz, 2 Hz)

Mass spectrum m/e: 436 (M+), 403, 377

(d) To a solution of 500 mg of 24,24-difluoro-5,7-cholestadiene-3β,25-diol (IIb) in 5 ml of pyridine, 2 ml of acetic anhydride was added. After standing overnight at room temperature, the reaction mixture was poured into 30 ml of 2 N hydrochloric acid and extracted with ethyl acetate. The separating organic layer was washed sequentially with 2 N hydrochloric acid, water, saturated aqueous sodium bicarbonate and saturated aqueous sodium chloride, and dried over anhydrous sodium sulfate. By distilling the solvent off, 3β-acetoxy-24,24-difluoro-5,7-cholestadien-25-ol (IIa) was obtained.

UV spectrum $\lambda_{max}$ (C$_2$H$_5$OH): 262, 272, 282, 294 nm

This invention is now described in greater detail by reference to the following examples which are given here for illustrative purposes only and are by no means intended to limit the scope of the invention.

EXAMPLE 1

A solution of 3 mg of 24,24-difluoro-5,7-cholestadiene-1α,3β,25-triol (IIb) in 300 ml of ether was exposed to a 200 W high pressure immersion mercury lamp through a Vycor filter at 0° C. in an argon stream under stirring. The reaction mixture was concentrated under vacuum at 20° C., and the resulting residue was purified by preparative high-pressure liquid chromatography to obtain 370 μg of 24,24-difluoro-1α,25-dihydroxyprevitamin D$_3$ [UV spectrum $\lambda_{max}$(EtOH): 261 nm]. All of the previtamin D$_3$ was dissolved in 2 ml of benzene, and the solution was heated under reflux in an argon stream for 2.5 hours. The reaction mixture was concentrated under vacuum at 20° C., and the resulting residue was purified by preparative high-pressure liquid chromatography, whereby 28 μg of previtamin D$_3$ (starting material) was recovered and 172 μg of 24,24-difluoro-1α,25-dihydroxyvitamin D$_3$ was obtained.

UV spectrum $\lambda_{max}$ (EtOH): 266 nm

NMR spectrum δ (CDCl$_3$): 0.56 (3H,s), 0.95 (3H,d,J=5 Hz), 1.31 (6H,s), 4.20 (1H,m), 4.40 (1H,m), 5.02 (1H,bs), 5.34 (1H,bs), 6.05 (1H,d,J=11 Hz), 6.38 (1H,d,J=11 Hz)

Mass spectrum m/e: 452 (M+), 434, 134

EXAMPLE 2

Five milligrams of 1α,3β-diacetoxy-24,24-difluoro-5,7-cholestadien-25-ol (IIa) obtained in Reference Example 5(f) was UV-irradiated and isomerized in the same manner as in Example 1. The resulting 1α-acetoxy-24,24-difluoro-25-hydroxyvitamin D$_3$ 3β-acetate was dissolved in 5 ml of ethanol. To the solution, 50 μl of 25% aqueous potassium hydroxide was added, and the mixture was deacetylated by heating under reflux for 30 minutes. After cooling, the reaction mixture was poured into a mixture of chloroform and water. The separating organic layer was washed with water, and dried over anhydrous sodium sulfate. After distilling the solvent off, the residue was purified by preparative high-pressure liquid chromatography to obtain 198 μg of 24,24-difluoro-1α,25-dihydroxyvitamin D$_3$. The produce had a UV spectrum and NMR spectrum that agreed with those of the compound prepared in Example 1.

EXAMPLE 3

A solution of 65 mg of 24,24-difluoro-5,7-cholestadiene-3β,25-diol (IIb) in 200 ml of diethyl ether was exposed to a 200 W high pressure immersion mercury lamp for 7.5 minutes through a Vycor filter in an argon stream under cooling. The solvent was distilled off under vacuum, and the residue was subjected to column chromatography (45 g of Sephadex LH-20) and eluted with a mixture of chloroform hexane (1:1), whereupon 25 mg of 24,24-difluoro-25-hydroxyprevitamin $D_3$ (having a maximum ultraviolet absorption at 260 nm in ether solution) was obtained and 16.6 mg of tachysterol and 4.9 mg of 24,24-difluoro-5,7-cholestadiene-3β,25-diol (IIb) used as starting material were recovered.

All of the resulting 24,24-difluoro-25-hydroxyprevitamin $D_3$ was dissolved in 10 ml of benzene, and the solution was heated under reflux in an argon stream for 1.5 hours. After standing at room temperature for 5 days, the solvent was distilled off under vacuum. The resulting residue was subjected to column chromatography (40 g of Sephadex LH-20) and eluted with a mixture of chloroform hexane (1:1), whereupon 0.25 mg of 24,24-difluoro-25-hydroxyvitamin $D_3$ was obtained.

UV spectrum $\lambda_{max}$ (95% $C_2H_5OH$): 265 nm

NMR spectrum δ ($CDCl_3$): 0.56 (3H,s), 0.95 (3H,d,J=6 Hz), 1.32 (6H,s), 3.95 (1H,m), 4.85 (1H,bs), 5.08 (1H,bs), 6.16 (2H, ABq,J=11 Hz)

EXAMPLE 4

Ninety-five milligrams of 3β-acetoxy-24,24-difluoro-5,7-cholestadien-25-ol (IIa) was UV-irradiated and isomerized in the same manner as in Example 3. The resulting 24,24-difluoro-25-hydroxyvitamin $D_3$ 3β-acetate was dissolved in 50 ml of ethanol. To the solution, 0.1 ml of 25% aqueous potassium hydroxide was added, and the mixture was deacetylated by heating under reflux for 30 minutes. After cooling, the reaction mixture was poured into a mixture of chloroform and water. The separating organic layer was washed with water, and dried over anhydrous sodium sulfate. After distilling the solvent off under vacuum, the residue was subjected to column chromatography (40 g of Sephadex LH-20) and eluted with a mixture of chloroform/hexane (1:1), whereupon 20.1 mg of 24,24-difluoro-25-hydroxyvitamin $D_3$ was obtained. The product had a UV spectrum and NMR spectrum that agreed with those of the compound prepared in Example 3.

What is claimed is:

1. A provitamin $D_3$ derivative of the formula:

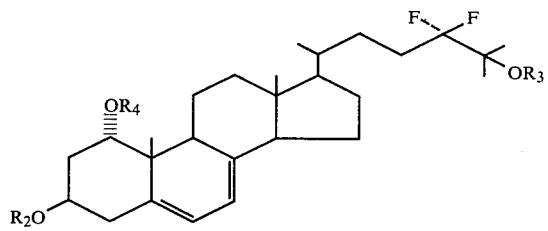

wherein $R_2$, $R_3$ and $R_4$ may be the same or different and represent hydrogen or a hydroxyl-protecting group.

2. A steroid derivative of the formula:

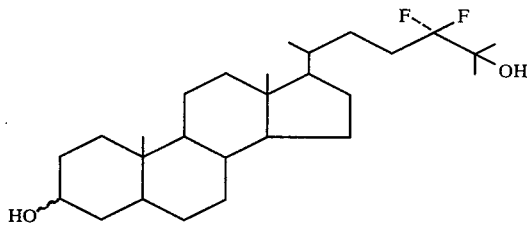

* * * * *

UNITED STATES PATENT AND TRADEMARK OFFICE
CERTIFICATE OF CORRECTION

PATENT NO. : 4,284,577
DATED : August 18, 1981
INVENTOR(S) : YAMADA et al

It is certified that error appears in the above–identified patent and that said Letters Patent are hereby corrected as shown below:

On The Title Page, Item (73) should read

-- [73] Assignees: "Hiroaki Takayada" should read --Hiroaki Takayama--

Signed and Sealed this

Thirtieth Day of March 1982

[SEAL]

Attest:

Attesting Officer

GERALD J MOSSINGHOFF

Commissioner of Patents and Trademarks